United States Patent [19]

Quack et al.

[11] 4,237,243

[45] Dec. 2, 1980

[54] USE OF CROSS-LINKED POLYMERS TO INCREASE THE VISCOSITY IN COSMETIC, PHARMACEUTICAL AND TECHNICAL COMPOSITIONS

[75] Inventors: Jochen M. Quack, Kelkheim; Alwin Reng, Frankfurt am Main; Juliane Balzer, Frankfurt am Main; Friedrich Engelhardt, Frankfurt am Main; Joachim Ribka, Offenbach am Main, all of Fed. Rep. of Germany

[73] Assignee: Hoechst Aktiengesellschaft, Fed. Rep. of Germany

[21] Appl. No.: 10,519

[22] Filed: Feb. 9, 1979

[30] Foreign Application Priority Data

Feb. 14, 1978 [DE] Fed. Rep. of Germany ....... 2806098

[51] Int. Cl.$^3$ ........................... C08F 8/12; C08F 8/28; C08F 8/44
[52] U.S. Cl. .................................... 525/154; 525/158; 525/162; 525/332; 525/336; 525/369; 525/385; 526/209; 526/210; 526/212
[58] Field of Search ...................... 525/369, 336, 154; 526/209, 210, 212

[56] References Cited

U.S. PATENT DOCUMENTS

| | | | |
|---|---|---|---|
| 3,247,171 | 4/1966 | Walker et al. | 525/369 |
| 3,784,597 | 1/1974 | Fujimoto et al. | 525/369 |
| 4,146,690 | 3/1979 | Togo et al. | 525/369 |

FOREIGN PATENT DOCUMENTS

1042233 10/1958 Fed. Rep. of Germany .
1368030 9/1974 United Kingdom .

*Primary Examiner*—William F. Hamrock
*Attorney, Agent, or Firm*—Connolly and Hutz

[57] ABSTRACT

Use of cross-linked polymers for increasing the viscosity in cosmetic, pharmaceutical and technical compositions, wherein the polymer chains have the following composition:

k - p molar % of groups of the formula

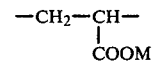

p molar % of groups of the formula

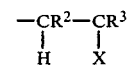

from 0 to 45 molar % of groups of the formula

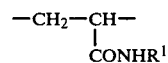

and
from 0.1 to 20 molar % of a cross-linking agent, wherein
$R^1$ represents as a statistical mean value from 0 to 100 molar % of hydrogen and from 100 to 0 molar %, each calculated on the proportion of (k-p) molar %, of $CH_2OH$ groups,
$R^2$ and $R^3$ are hydrogen, or one of the radicals $R^2$ and $R^3$ is methyl, the other being hydrogen,
X is cyano, alkoxycarbonyl with from 1 to 8 carbon atoms altogether, whose alkoxy radical may also be substituted by —OH, alkanoyloxy with from 2 to 6 carbon atoms, alkanoylamino with 2 to 8 carbon atoms which—if they have at least 4 carbon atoms—may also be cyclic and then form a pyrrolidone or caprolactam ring, phenyl, carboxyl or trialkoxysilyl with 1 to 2 carbon atoms in the alkoxy groups,
M is an alkali metal cation, and
k stands for the range of from 99.9 to 50,
p stands for the range of from 5 to k,
said products being prepared by copolymerizing, calculated on the total molar amount of all monomers,
k molar % of acrylamide, k being defined as above,
from 0 to 45 molar % of a compound of the formula I

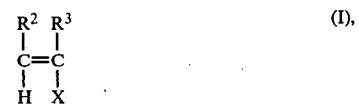

in which $R^2$, $R^3$ and X are defined as above, and from 0.1 to 20 molar % of a cross-linking agent in the presence of a radical initiator in a water-miscible alkanol, mixing the polymer dispersion obtained under the action of strong shearing forces with p molar % of an alkali metal hydroxide of the formula MOH, p being defined as above, heating the mixture at a temperature of from 30 to 150° C. up to the saponification of p molar % of amide groups to form —COOM— groups, and either isolating the copolymer obtained or methylolating the same, after removing the ammonia, in a lower alkanol with from 0 to (k-p) molar % of paraformaldehyde, k and p being defined as above, at a temperature of from 10° C. to the boiling point of the lower alkanol employed.

8 Claims, No Drawings

USE OF CROSS-LINKED POLYMERS TO INCREASE THE VISCOSITY IN COSMETIC, PHARMACEUTICAL AND TECHNICAL COMPOSITIONS

The present invention relates to the use of crosslinked polymers to increase the viscosity in cosmetic, pharmaceutical and technical compositions.

Aqueous and solvent-containing polynary systems, such as solutions, emulsions or suspensions, are frequently adjusted to a higher viscosity for application technology or economical reasons or also for reasons of stability. Thus, it is possible, for example, to considerably increase the stability of emulsions, suspensions or gels depending on the storage period and storage temperature by increasing the viscosity of the internal or external phases. Another advantage is the improved distributability due to the increase in viscosity, for example, of skin cosmetics or pharmaceutical ointments on the skin surface. In the case of technical compositions, for example wallpaper or paint removers, a high viscosity involves advantages due to an improved adhesion of said compositions on the ground to be treated, which results in a more regular distribution and an increased effectiveness. Besides these advantages with regard to application, the high viscosity of these compositions also involves additional advantages in manufacture, handling, packaging, storing as well as in transport.

It may be stated generally that the influence on the rheological behavior in the preparation of cosmetic, pharmaceutical and technical compositions is an important factor for the use of these products in practice.

In technical literature a great number of so-called thickening agents have been described which are to alter the rheological properties of polynary systems, such as emulsions, suspensions and solutions. There have been known, for example, cellulose ether, gelatin, or sodium alginate, in order to increase the viscosity of aqueous systems; and there may also be employed fatty acid-polyethylene-glycol mono- or diesters, highly dispersed amorphous silicic acid, polymers and similar substances, by themselves or in combination.

However, these so-called thickening agents show various drawbacks when applied. Thus, the compositions prepared with cellulose ethers are susceptible to bacteria and when applied yield unpleasant "stringing" gels, whereas fatty acid-polyethylene-glycol esters cause turbidity due to hydrolysis taking place in the presence of water, and inorganic thickening agents, such as highly dispersed amorphous silicic acid, may result in precipitates in the ready-made formulations. Thickening agents of natural origin, for example, agar-agar or tragacanth, have the drawback that they show a varying composition depending on their origin.

It has also been known that aqueous highly viscous compositions and/or gels may be prepared by the copolymerization of acrylamide with polyunsaturated compounds in aqueous solution. The products thus obtained are still capable of swelling in water, but no longer soluble. For example, in U.S. Pat. No. 3,210,310 and French Pat. No. 1 411 944, so-called soil stabilizers have been mentioned which are prepared by way of polymerization of the aqueous monomer solutions in the soil formation to be stabilized. By the drying and grinding of aqueous gels prepared in this manner, pulverulent products are obtained, however, which show only an insignificant swelling and thus thickening power in water.

It has also been proposed before to prepare water-insoluble copolymers which are swellable in water, however, in a solid form by way of precipitation polymerization in organic solvents, while using as starting materials (a) compounds containing at least two olefinically unsaturated polymerizable groups, such as ethanediol diacrylate or divinylbenzene,
(b) water-soluble polymerizable compounds, such as acrylic acid or acrylamide and, optionally,
(c) water-insoluble monomers, such as methyl methacrylate or styrene.

However, in the course of this process inhomogeneous polymers are obtained which contain particles of a different swelling power. From German Patent Specification No. 1 042 233 cross-linked copolymers are known which contain via a polymerization process at least 25% by weight of a lower aliphatic, $\alpha,\beta$-unsaturated carboxylic acid or of an anhydride of a lower aliphatic unsaturated polycarboxylic acid, from 0 to 75% by weight of a monoolefinic monomer which differs from the former, and from 0.1 to 30%, calculated on the weight of the carboxylic acid and/or the carboxylic acid anhydrides, of a polyvinyl ether, a polyallyl ether or a polycrotyl ether of a polyvalent alcohol having at least 4 carbon atoms and at least 3 OH groups in the molecule. A serious drawback of this known process is to be seen in the fact that it leads only to polymers with free carboxyl groups. These compounds have only a limited water-binding power, however, i.e. they are capable of swelling but to a relatively low degree. In order to obtain substances showing a high swelling power, it is necessary to treat the polymers, which have been prepared according to the known process and which frequently display a tough caoutchouc-like condition, with alkali. In the course of this process a jelly is obtained which may be adjusted to the desired viscosity by adding an additional amount of water. This complicated process represents a considerable drawback when using these known thickening agents. Another difficulty involved in the use of the known thickening agents resides in the fact that said agents may not be converted completely into the salts, but only to a determined and defined fraction, in order to produce their activity at a maximum. This fact involves the considerable difficulty that in the treatment process the alkali being present in a proportion short of that of the carboxyl groups must gradually diffuse from the outside into a pre-swollen cross-linked polymer. This process is not only time-consuming, but also necessarily involves an irregular neutralization degree of the polymer particle, in that the degree is reduced from the outside to the inside. As a result, the swelling power is not optimum, and the thickening obtained with the products is characterized by a granular irregular structure. Even the thickening effect of the known products is irregular and relatively insignificant, due to the difficulties involved in their application. Apart from the drawbacks in view of the application of the cross-linked copolymers which may be prepared according to German Patent Specification No. 1 042 233, the preparation process itself shows deficiencies and difficulties with regard to technology which may involve risks and disturbances especially when operating on an industrial scale. For due to the use of monomeric acrylic acid in the copolymerization process, the known process may only be carried out in relatively low-boiling hydrocarbons which are known to have a very low flash point and which are therefore not preferred as solvents in industry. Furthermore, the copolymerization frequently yields very fine-grained, almost muddy polymers whose filtration is not always easy, but which often obstruct the pores of the filters, thus causing disturbances of the production process.

It has now been found that use may be made of cross-linked polymers as viscosity-increasing agents, whose polymer chains show the following composition:

k-p molar % of groups of the formula

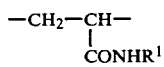

p molar % of groups of the formula

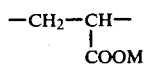

from 0 to 45 molar % of groups of the formula

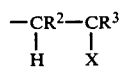

and
from 0.1 to 20 molar % of a cross-linking agent, wherein
$R^1$ represents as a statistical mean value from 0 to 100 molar % of hydrogen and from 100 to 0 molar %, each calculated on the proportion of (k-p) molar %, of $CH_2OH$ groups,
$R^2$ and $R^3$ are hydrogen, or one of the radicals $R^2$ and $R^3$ is methyl, the other being hydrogen,
X is cyano, alkoxycarbonyl with from 1 to 8 carbon atoms altogether, whose alkoxy radical may also be substituted by —OH, alkanoyloxy with from 2 to 6 carbon atoms, alkanoylamino with 2 to 8 carbon atoms which—if they have at least 4 carbon atoms—may also be cyclic and then form a pyrrolidone or caprolactam ring, phenyl, carboxyl or trialkoxysilyl with 1 to 2 carbon atoms in the alkoxy groups,
M is an alkali metal cation, and
k stands for the range of from 99.9 to 50,
p stands for the range of from 5 to k,
said products being prepared by copolymerizing, calculated on the total molar amount of all monomers,
k molar % of acrylamide, k being defined as above,
from 0 to 45 molar % of a compound of the formula I

in which $R^2$, $R^3$ and X are defined as above, and from 0.1 to 20 molar % of a cross-linking agent in the presence of a radical initiator in a water-miscible alkanol, mixing the polymer dispersion obtained under the action of strong shearing forces with p molar % of an alkali metal hydroxide of the formula MOH, p being defined as above, heating the mixture at a temperature of from 30° to 150° C. up to the saponification of p molar % of amide groups to form —COOM— groups, and either isolating the copolymer obtained or methylolating the same, after removing the ammonia, in a lower alkanol with from 0 to (k-p) molar % of paraformaldehyde, k and p being defined as above, at a temperature of from 10° C. to the boiling point of the lower alkanol employed.

Examples for compounds of the formula I, which may be employed in the copolymerization, are the following compounds: Acrylonitrile, methacrylonitrile, crotonic acid nitrile,
methyl-, ethyl-, β-hydroxyethyl-, propyl-, β-hydroxypropyl-, isopropyl-, (n)butyl-, isobutyl-, sec.butyl-, tert.butyl-, pentyl-, hexyl-, 2-ethyl-hexyl-acrylate;
methyl-, ethyl-, β-hydroxyethyl-, propyl-, β-hydroxypropyl-, isopropyl-, (n)butyl-, isobutyl-, sec.butyl-, tert.butyl-, pentyl-, hexyl-, 2-ethyl-hexyl-methacrylate;
pentyl-, hexyl-, 2-ethyl-hexyl-methacrylate;
methyl-, ethyl-, propyl-, isopropyl-, (n)butyl-, 2-ethylhexyl-crotonate;
vinyl acetate, vinyl propionate, vinyl butyrate, vinyl capronate,
3-allyl(Δ1,2)-acetate, -propionate, -butyrate;
N-vinyl-acetamide, -propionamide, -butyramide;
N-vinyl-pyrrolidone, -piperidone, -caprolactam;
styrene, trimethoxysilylethylene, triethoxysilylethylene, 1- or 3-trimethoxysilyl-propylene(Δ1,2), 1- or 3-triethoxysilylpropylene(Δ1,2).

If in the copolymerization there also used compounds of the formula I, preference is given to those in which $R^2$ is hydrogen, $R^3$ is hydrogen or methyl and X is cyano, alkoxycarbonyl of from 1 to 8 carbon atoms, whose alkoxy radical may also be substituted by —OH, acetoxy, N-pyrrolidonyl, phenyl or triethoxysilyl.

With regard to the properties of the above compounds when using the latter as viscosity-increasing agents and with regard to the price of the products, it is advantageous to use at most 20%, however, in particular none at all, of the compounds of the formula I in the copolymerization.

Another preferred group of cross-linked copolymers is characterized in that p has a value of from 30 to 70, i.e that the polymers contain from 30 to 70 molar % of —COOM— groups, calculated on the total molar number of the copolymerized monomers. The preferred copolymers of this kind are distinguished by an optimum thickening effect with a minimum sensitiveness to electrolyte at the same time.

As cross-linking agents there are used in the copolymerization olefinically polyunsaturated compounds, such as divinyl benzene, tetraallyloxethane, diallyl ethers or ally ethers of polyfunctional alcohol components, for example di- and triallyl-glyceric ethers as well as allyl ethers which are derived from alcohols of the sugar series, for example from erythritol, pentaerythritol, arabitol, mannitol, sorbitol or from glucose. Particularly suitable are polyglyceric polyally ethers of the general formula II

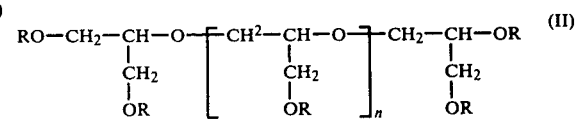

in which
n stands for a number of from 0 to 30, preferably from 1 to 10, and

R represents hydrogen for 70 to 5% and represents groups of the formulae —CH$_2$—CH=CH$_2$ or —CH$_2$—C(CH$_3$)=CH$_2$ for 95 to 30%.

Polyglyceric polyallyl ethers of this kind are obtained in a manner known per se by the reaction of polyglycerols—which have been prepared, for example, by a polycondensation of glycide—with allyl chloride or methallyl chloride.

The polymerization of the acrylamide of the compound of the formula I and the cross-linking agent is effected in a water-soluble alkanol of from 1 to 4 carbon atoms, such as methanol, ethanol, propanol, isopropanol, preferably in tert.butanol, as solvent.

The water content of the lower alkanols employed as solvents should not exceed 10% by weight, for otherwise a lump formation may occur in the polymerization. The process is preferably carried out at a water content of from 0 to 5%.

The amount of the solvent to be employed depends to a certain degree on the type of the comonomers used. As a rule, from 200 to 1000 g of the solvent are used per 100 g of total monomer.

As usual, the polymerization is carried out under a protective atmosphere, preferably under a nitrogen blanket. The polymerization temperature is in the range of from 20° to 120° C., preferably from 40° to 80° C.

To start the polymerization, use may be made of the common polymerization initiators, for example organic peroxides, such as benzoyl peroxide, tert.butyl hydroperoxide, methylethyl-ketone peroxide, or cumol hydroperoxide. There may also be used advantageously azo compounds, such as azo-di-iso-butyro-nitrile. Above all redox systems which contain as reducing component aliphatic and aromatic sulfinic acids, such as benzene-sulfinic acid and toluene-sulfinic acid or derivatives of these acids, for example Mannich adducts from sulfinic acids, aldehydes and amino compounds, as they have been described in German Patent Specification No. 1 301 566, have proved to be advantageous. Per 100 g of total monomer there are used as a rule from 0.05 to 2 g of the polymerization initiator.

When carrying out the copolymerization in the manner described, polymer pastes are obtained which may well be stirred and which are suitable without problems for the subsequent reaction with alkali metal hydroxides. Of course it is also possible to isolate the copolymer obtained intermediately, for example by suction-fitration and washing with the solvent used.

The polymer paste obtained in the polymerization, which usually shows a slightly granular structure, is at first subjected to strong shearing forces in an appropriate apparatus, for example by stirring with a high-speed stirrer (Ultra-Turrax) or by grinding in a PUC mill, until the suspension shows a completely regular flow behavior; thereafter the desired amount of the alkali metal hydroxide is added, while the vigorous mixing is continued, in which process a further addition of from 0 to 200 ml of the solvent used—calculated on 100 g of copolymer—may be required, depending on the mixing or grinding aggregate used. The mixture of the polymer dispersion with the metal hydroxide obtained in the above manner is subsequently heated, while stirring, at a temperature of from 30° to 150° C., until the desired degree of saponification is reached. In order to prepare a copolymer with p molar % of —COOM— groups, there are also used p molar % of the alkali metal hydroxide for the saponification. The preferred saponification temperature is in the range of from 50° to 100° C. It is particularly advantageous to carry out the saponification at the boiling temperature of the reaction mixture at the reflux condenser. The alkali metal hydroxide is added to the copolymer dispersion suitably in finely ground form. As alkali metal hydroxides there are preferred sodium hydroxide and potassium hydroxide. Under these reaction conditions the saponification takes from about 1 to 6 hours.

By using different amounts of alkali metal hydroxide it is possible to prepare polymers with different degrees of saponification, i.e. different contents of carboxylate groups. In order to arrive at a high swelling power in water and/or an optimum thickening effect, polymers with a saponification degree in the range of from 90 to 20%, preferably from 30 to 60%, have proved to be most suitable.

The described process may also be carried out in principle without the action of strong shearing forces on the copolymer dispersion before and during the addition of alkali. However, operating under the action of the shearing forces is particularly preferred, because the products prepared in accordance with this embodiment not only yield thickening agents being far more homogeneous, but they are also about 10 times as effective as products which have been prepared without employing strong shearing forces.

This effect of the application of strong shearing forces in the preparation of the copolymers is particularly surprising, as it has been known that the action of strong shearing forces on polyacrylamides leads to a sudden reduction of the average molecular weight and thus to a drastic reduction in viscosity (cf. for example, A. B. Bestul, Journal of Chemical Physics, volume 24, pages 1196 to 1201, Journal of Applied Physics, volume 25, pages 1069 to 1074). The fact that operating under the action of strong shearing forces leads to products having considerably improved properties represents the special value of this preferred process measure.

If cross-linked copolymers are to be prepared in which $R^1$ represents hydrogen to 100%, the copolymer is isolated after completion of the saponification reaction, either by evaporating the solvent used or by filtering off the dispersion with suction and subsequently washing the polymer with the solvent used or with a more volatile lower alkanol, and is afterwards dried, preferably in vacuo, at a temperature of from 40° to 80° C. In this manner a pulverulent copolymer is obtained which shows the above composition.

In order to prepare cross-linked copolymers in which R represents on a statistical average the methylol group to a certain percentage, i.e. copolymers whose amide groups are completely or partially methylolated, the copolymers obtained after the saponification are reacted in a water-soluble alkanol of from 1 to 4 carbon atoms with the amount of paraformaldehyde corresponding to the desired degree of methylolation. For this reaction there may be used the copolymers that have been prepared according to the invention and have been isolated after the saponification. For this purpose they are suspended in 3 to 10 times the amount by weight of the alkanol employed as solvent thereafter the calculated amount of paraformaldehyde is added, and the mixture is methylolated at a temperature in the range of from 10° C. to the boiling point of the alkanol employed as solvent.

If copolymers are to be prepared in which $R^1$ is —CH$_2$OH to 100%, i.e. all carbonamide groups available are to be methylolated, it is also possible to use an excess amount of paraformaldehyde of up to 20%.

In this connection the reaction period depends on the reaction temperature, and in order to arrive at economical reaction times it is advantageous to carry out the methylolation at a temperature in the range of from 40° C. to the boiling point of the solvent, in particular from 50° to 60° C.

For the preparation of methylolated copolymers, however, it is in no way required to isolate the copolymers after saponification, but the polymer dispersions obtained in the saponification step may rather be processed directly, if care is taken that the ammonia formed in the saponification process is removed from the reaction mixture. In the simplest case this may be performed by distilling off part of the alkanol employed as solvent. A concentration of the polymer dispersion that is too strong may be avoided by adding fresh solvent, and the separation of the ammonia can also be completed by another or the repeated addition of fresh solvent and removal by distillation.

An equally suitable variant of the methylolation process consists in allowing the reaction mixture—after having added the paraformaldehyde—to react over night at room temperature.

The polymers prepared in the manner described above shows an extremely high swelling power in aqueous and/or solvent-containing systems and are therefore particularly appropriate to increase the viscosity of cosmetic, pharmaceutical and technical compositions in the form of polynary systems, such as emulsions, suspensions or solutions which contain, for example, water, glycerol, alcohol, propylene-glycol, polyglycols or non-ionic surfactants. Also combinations with other thickening agents, such as cellulose ether, highly dispersed amorphous silicic acids or other polymers, are possible.

As compared with the known polymers being present in the form of the free acid, the above-described polymers have the advantage that owing to the immediate adjustment of the final viscosity it is possible to considerably reduce the period of preparation. Besides, in the case of the latter no subsequent neutralization is required, so that there is no risk that there are free acid groups which have not yet been neutralized.

In the following Tables 1 and 2 the proportions of the groups

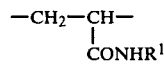

which are contained in the polymers, with $R^1$ being hydrogen and R HD 1 being —$CH_2OH$, are calculated each on the total polymer molecule. If from these data (columns "$R^1=H$" and "$R^1=CH_2OH$") there are to be calculated the statistical proportions $A_H$ of the radicals $R^1$ representing hydrogen and $A_F$ of those representing —$CH_2OH$, calculated on the proportion of k-p molar %, the following relations are applicable:

$$A_H = \frac{(\text{specification of column } "R^1 = H") \cdot 100}{(\text{specif. of col. } "R^1 = H") + (\text{specif. of col. } "R^1 = -CH_2OH")}$$

$$A_F = \frac{(\text{specification of column } "R^1 = -CH_2OH") \cdot 100}{(\text{specif. of col. } "R^1 = H") + (\text{specif. of col. } "R^1 = -CH_2OH")}$$

For the cross-linking agents employed, the following abbreviations have been used in Tables 1 and 2:
A = polyglycide-allyl ether
B = polyglycide-methallyl ether
C = polyglucose-methallyl ether
D = tetraallyl oxethane
E = trisacrylolylperhydro-s-triazine
F = butane-diol dimethacrylate.

The following Examples serve to illustrate the invention.

EXAMPLE 1

440 Milliliters of tert.butanol and 16 ml of de-ionized water are introduced into a reaction vessel provided with stirrer, reflux condenser, thermometer, gas inlet pipe, dropping funnel and a water bath to be heated electrically, and in said mixture 71 g of acrylamide are dissolved, while stirring. Thereafter 0.7 g of a polyallyl ether is added to this solution, the polyally ether having been prepared by reacting a polyglycerol having a molecular weight of 1270 and an OH number of 680 with allyl chloride in an aqueous alkaline medium.

While introducing a slight nitrogen current, the monomer solution is stirred, and the temperature is brought to 50° C. by means of the electric water bath. At this temperature, a solution of 1.0 g of azodiisobutyronitrile in 70 ml of tert.butanol is added dropwise via a dropping funnel in the course of 15 minutes. About 5 minutes after the catalyst addition has been completed the polymerization reaction starts. In this process the polymer precipitates as a white pulpy mass, the temperature increasing within 30 minutes up to 79° C. Upon completion of the polymerization, i.e. when the reaction temperature is falling, the heating is continued for another 2 hours at a bath temperature of 90° C., while stirring.

After cooling of the reaction mixture to 30°–40° C., the reaction flask is provided with a homogenizer, or the polymer dispersion is pumped over via a homogenizer.

Under the action of strong shearing forces 20 g of NaOH in a pulverulent form as well as from 100 to 200 ml of tert.butanol are then added, whereupon a homogeneous white dispersion is formed which can well be stirred and which is now heated under reflux for 4 hours, while ammonia is split off.

For isolation of the copolymer, the homogeneous white polymer dispersion obtained is either filtered off with suction and the polymer is subsequently dried in vacuo, or the tert.butanol employed as reaction medium is distilled off in vacuo, while stirring.

In both cases the polymer with $p \approx 50$ molar % and $k \approx 50$ molar % is obtained in the form of a porous white powder. The yield is 91 g (100% of the theory).

These polymers show in water an extremely high swelling power and may therefore be used as thickening agents.

A 0.2% aqueous composition of a polymer thus prepared has at 25° C. a viscosity of 3200 cp.

If in an analogous polymer mixture there are used as a catalyst system
0.7 g of dibutylamine hydrochloride,
0.1 g of the compound

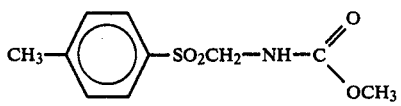

0.2 g of (NH$_4$)$_7$S$_2$O$_8$,
a polymer is obtained in an equally high yield which shows in a concentration of 0.2% in water at 25° C. a viscosity value of 3300 cp.

In a manner analogous to that of Example 1, the copolymers of the composition given in Table 1 may also be prepared.

are distilled off from the reaction mixture in vacuo at 60° C., while stirring.

Subsequently 20 g of paraformaldehyde are added, while stirring continuously, and after 2 hours the stirring is continued at 50° C. Thereafter the copolymer obtained, which is practically methylolated to 100%, is worked up as has been described in Example 1.

The yield is 97 g (90% of the theory).

A 0.2% aqueous composition of the copolymer obtained has a viscosity of 300 cp at 25° C.

EXAMPLE 3

50 Grams of the pulverulent copolymer obtained according to Example 1 are suspended in 120 ml of

TABLE 1

| No. | —CH$_2$—CH— CONHR$^1$ R$^1$ = H [molar %] | —CH$_2$—CH— CONHR$^1$ R$^1$ = —CH$_2$OH [molar %] | —CH$_2$—CH— COOM [molar %] | R$^2$ | R$^3$ | —C—C— H X, X | Cross-linking molar % | agent molar % | Yield [% of the theory] | Viscosity [cp] | Ball | Content of the measured solution |
|---|---|---|---|---|---|---|---|---|---|---|---|---|
| 1 | 86.95 | — | 6.05 | — | — | — | — | F 7 | 100 | 27 | 3 | 0.2 |
| 2 | 78.30 | — | 11.7 | — | — | — | — | E 10 | 100 | 16 | 3 | 0.1 |
| 3 | 40.85 | — | 54.15 | — | — | — | — | C 5 | 100 | 64 | 3 | 0.1 |
| 4 | 7.50 | — | 89.99 | — | — | — | — | C 2.5 | 100 | 240 | 3 | 0.2 |
| 5 | — | — | 98 | — | — | — | — | C 2 | 100 | 580 | 3 | 0.2 |
| 6 | 32.77 | — | 54.15 | H | H | —CO$_2$CH$_3$ | 8.07 | D 5 | 100 | 70 | 3 | 0.1 |
| 7 | 24.00 | — | 53.01 | H | H | —CO$_2$CH$_3$ | 15.99 | E 7 | 100 | 66 | 3 | 0.1 |
| 8 | 33.64 | — | 55.58 | H | H | —CO$_2$H$_5$ | 8.28 | D 2.5 | 100 | 340 | 3 | 0.1 |
| 9 | 25.02 | — | 55.29 | H | H | —CO$_2$H$_5$ | 16.88 | D 3 | 93 | 150 | 3 | 0.1 |
| 10 | 33.81 | — | 55.86 | H | H | CO$_2$C$_4$H$_9$ | 8.33 | D 2 | 96 | 990 | 3 | 0.1 |
| 11 | 24.51 | — | 48.55 | H | H | —CO$_2$C$_4$H$_9$ | 16.34 | F 5 | 91 | 140 | 3 | 0.1 |
| 12 | 33.98 | — | 56.14 | H | H | —CO$_2$CH$_2$CH(C$_2$H$_5$)(CH$_2$)$_3$CH$_3$ | 8.37 | B 1.5 | 97 | 2000 | 3 | 0.1 |
| 13 | 25.02 | — | 55.29 | H | H | —CO$_2$CH$_2$CH(C$_2$H$_5$)(CH$_2$)$_3$CH$_3$ | 16.88 | A 3 | 91 | 420 | 3 | 0.1 |
| 14 | 31.05 | — | 51.30 | H | H | —CN | 7.65 | D 10 | 100 | 16 | 3 | 0.1 |
| 15 | 23.22 | — | 51.30 | H | H | —CN | 15.48 | E 10 | 100 | 81 | 3 | 0.2 |
| 16 | 33.47 | — | 55.29 | H | CH$_3$ | —CO$_2$—C$_2$H$_4$OH | 7.90 | F 3 | 98 | 200 | 3 | 0.1 |
| 17 | 25.54 | — | 56.43 | H | CH$_3$ | —CO$_2$C$_2$H$_4$OH | 17.02 | C 1 | 94 | 967 | 3 | 0.2 |
| 18 | 16.77 | — | 55.57 | H | H | —CO$_2$CH$_2$CH(C$_2$H$_5$)(CH$_2$)$_3$CH$_3$ | 25.16 | F 2.5 | 100 | 248 | 3 | 0.2 |
| 19 | 8.16 | — | 54.72 | H | H | —CO$_2$CH$_2$CH(C$_2$H$_5$)(CH$_2$)$_3$CH$_3$ | 33.12 | B 4 | 94 | 50 | 3 | 0.2 |
| 20 | — | — | 45.60 | H | H | —CO$_2$CH$_2$CH(C$_2$H$_5$)(CH$_2$)$_3$CH$_3$ | 34.40 | F 20 | 87 | 9 | 2 | 0.2 |
| 21 | 27.60 | — | 45.60 | H | H | —O—COCH$_3$ | 6.80 | E 20 | 100 | 5 | 2 | 0.2 |
| 22 | 34.15 | — | 56.43 | H | H | —C$_6$H$_5$ | 8.41 | B 1 | 100 | 6800 | 5 | 0.2 |
| 23 | 23.22 | — | 51.30 | H | H | —C$_6$H$_5$ | 15.48 | F 10 | 100 | 9 | 3 | 0.2 |
| 24 | 34.15 | — | 56.43 | H | CH$_3$ | —CO$_2$CH$_3$ | 8.41 | B 1 | 100 | 5400 | 5 | 0.2 |
| 25 | 25.02 | — | 55.29 | H | CH$_3$ | —CO$_2$CH$_3$ | 16.68 | E 3 | 100 | 867 | 4 | 0.2 |
| 26 | 37.82 | — | 55.86 | H | H | —Si(C$_2$H$_5$O)$_3$ | 4.31 | A 2 | 100 | 977 | 4 | 0.2 |
| 27 | 33.46 | — | 55.29 | H | H | —Si(C$_2$H$_5$O)$_3$ | 8.24 | C 3 | 100 | 78 | 4 | 0.2 |
| 28 | 29.29 | — | 55.29 | H | H | —Si(C$_2$H$_5$O)$_3$ | 12.41 | B 3 | 100 | 163 | 4 | 0.2 |
| 29 | 24.25 | — | 53.58 | H | H | —Si(C$_2$H$_5$O)$_3$ | 16.17 | F 6 | 97 | 24 | 3 | 0.2 |
| 30 | 25.54 | — | 56.43 | H | H | —N(CH$_2$—CH$_2$)(CO—CH$_2$) | 17.02 | A 1 | 100 | 8293 | 5 | 0.2 |
| 31 | 60.20 | — | 26.14 | H | H | —COOH | 11.5 | B 1 | 100 | 601 | 4 | 0.2 |

EXAMPLE 2

Example 1 is repeated with the difference that the copolymer is not isolated after the 4-hour refluxing period. Instead of this measure, 200 ml of tert.butanol tert.butanol, while stirring. Subsequently 9 g of paraformaldehyde are added to the suspension, and the mixture is stirred for 2 hours at 50° C.

The polymer with $p \approx 50$ molar %, $k \approx 50$ molar % and a degree of methylolation of about 85% is worked up, as has been described in Example 1.

Yield: 58 g (98% of the theory).

The viscosity of the 0.2% aqueous composition at 25° C. is 3000 cp.

In a manner analogous to that of Examples 2 or 3, the valuable copolymers of the composition given in Table 2 may also be prepared.

The following Examples illustrate the possibilities of application of the polymers described in the preparation of cosmetic, pharmaceutical and technical compositions, for example in skin cosmetics, such as liquid or creamy oil-in-water or water-in-oil emulsions, liquid cream- or gel-like hair setting lotions, make-up preparations, toothpastes, hair creams, shampoos, hair dyes, shaving creams, hair forming preparations, sun protective agents or insect protective agents. Said polymers

TABLE 2

| No. | $-CH_2-CH-$ $\vert$ $CONHR^1$ $R^1 = H$ [molar %] | $R^1 = -CH_2OH$ [molar %] | $-CH_2-CH-$ $\vert$ $COOM$ [molar %] | $R^2$ | $R^3$ | $-rC-C-$ with $R^2$, $R^3$, H, X; X | Cross-linking agent molar % | mol-ar % | Yield [% of the theory] | Viscosity [cp] | Ball | Content of the measured solution |
|---|---|---|---|---|---|---|---|---|---|---|---|---|
| 1 | — | 50.50 | 46.99 | — | — | — | — | A 2.5 | 99 | 260 | 4 | 0.2 |
| 2 | 10.37 | 37.73 | 48.88 | — | — | — | — | B 3 | 98 | 250 | 4 | 0.2 |
| 3 | 19.50 | 27.72 | 51.77 | — | — | — | — | A 1 | 100 | 31000 | 6 | 0.2 |
| 4 | 37.62 | 5.94 | 55.44 | — | — | — | — | A 1 | 100 | 23000 | 6 | 0.2 |
| 5 | 40.09 | 2.97 | 55.93 | — | — | — | — | A 1 | 100 | 25000 | 6 | 0.2 |
| 6 | 23.75 | 11.21 | 52.25 | H | H | $-CO_2CH_3$ | 7.79 | D 5 | 100 | 79 | 3 | 0.1 |
| 7 | 24.37 | 11.50 | 53.62 | H | H | $-CO_2C_2H_5$ | 7.99 | D 2.5 | 100 | 178 | 3 | 0.1 |
| 8 | 15.68 | 22.54 | 51.94 | H | H | $-CO_2C_4H_9$ | 7.84 | D 2 | 96 | 537 | 3 | 0.1 |
| 9 | 15.84 | 22.77 | 52.47 | H | $CH_3$ | $-CO_2CH_3$ | 7.92 | B 1 | 100 | 5300 | 5 | 0.2 |
| 10 | 15.52 | 22.31 | 51.41 | H | $CH_3$ | $-CO_2C_2H_4CH$ | 7.76 | F 3 | 98 | 199 | 3 | 0.1 |
| 11 | 14.4 | 20.7 | 47.7 | H | H | $-CN$ | 7.2 | D 10 | 100 | 17 | 3 | 0.1 |
| 12 | 7.2 | 20.7 | 47.7 | H | H | $-CN$ | 14.4 | E 10 | 100 | 107 | 3 | 0.2 |
| 13 | 16.10 | 11.44 | 53.35 | H | H | $-CO_2CH_2CH(CH_2)_3CH_3$ with $C_2H_5$ | 16.10 | A 3 | 91 | 340 | 3 | 0.1 |
| 14 | — | 86.95 | 6.04 | H | — | — | — | F 7 | 100 | 27 | 3 | 0.2 |
| 15 | — | 78.3 | 11.70 | H | — | — | — | E 10 | 100 | 16 | 3 | 0.1 |
| 16 | — | 40.85 | 54.15 | H | — | — | — | F 7 | 100 | 64 | 3 | 0.2 |
| 17 | — | 7.50 | 89.99 | H | — | — | C 2.5 | 100 | 240 | 3 | 0.1 |
| 18 | — | — | 98 | H | — | — | — | C 2 | 100 | 580 | 3 | 0.2 |
| 19 | — | 32.77 | 54.15 | H | H | $-CO_2CH_3$ | 8.07 | D 5 | 100 | 70 | 3 | 0.1 |
| 20 | — | 23.99 | 53.01 | H | H | $-CO_2CH_3$ | 15.99 | E 7 | 100 | 66 | 3 | 0.1 |
| 21 | — | 33.63 | 55.57 | H | H | $-CO_2C_2H_5$ | 8.28 | D 2.5 | 100 | 340 | 3 | 0.1 |
| 22 | — | 25.02 | 55.29 | H | H | $-CO_2C_2H_5$ | 16.68 | D 3 | 93 | 150 | 3 | 0.1 |
| 23 | — | 33.81 | 49.98 | H | H | $-CO_2C_4H_9$ | 8.33 | D 2 | 96 | 990 | 3 | 0.1 |
| 24 | — | 24.51 | 54.15 | H | H | $-CO_2C_4H_9$ | 16.34 | F 5 | 91 | 140 | 3 | 0.1 |
| 25 | — | 33.98 | 56.14 | H | H | $-CO_2CH_2CH(CH_2)_3CH_3$ with $C_2H_5$ | 8.37 | B 1.5 | 97 | 2000 | 3 | 0.1 |
| 26 | — | 25.02 | 55.29 | H | H | $-CO_2CH_2CH(CH_2)_3CH_3$ with $C_2H_5$ | 16.68 | A 3 | 91 | 420 | 3 | 0.1 |
| 27 | — | 31.05 | 51.30 | H | H | $-CN$ | 7.65 | D 10 | 100 | 16 | 3 | 0.1 |
| 28 | — | 23.22 | 51.30 | H | H | $-CN$ | 15.58 | E 10 | 100 | 81 | 3 | 0.2 |
| 29 | — | 33.46 | 55.29 | H | $CH_3$ | $-CO_2C_2H_4OH$ | 8.24 | F 3 | 98 | 200 | 3 | 0.1 |
| 30 | — | 25.54 | 56.43 | H | $CH_3$ | $-CO_2C_2H_4OH$ | 17.02 | C 1 | 94 | 967 | 3 | 0.2 |
| 31 | — | 16.77 | 55.60 | H | H | $-CO_2CH_2CH(CH_2)_3CH_3$ with $C_2H_5$ | 25.15 | F 2.5 | 100 | 248 | 3 | 0.2 |
| 32 | — | 8.16 | 54.72 | H | H | $-CO_2CH_2CH(CH_2)_3CH_3$ with $C_2H_5$ | 34.15 | B 4 | 94 | 50 | 3 | 0.2 |
| 33 | — | — | 45.60 | H | H | $-CO_2CH_2CH(CH_2)_3CH_3$ with $C_2H_5$ | 34.40 | F 20 | 87 | 9 | 2 | 0.2 |
| 34 | — | 27.60 | 45.60 | H | H | $-O-COCH_3$ | 6.80 | E 20 | 100 | 5 | 2 | 0.2 |
| 35 | — | 34.15 | 54.55 | H | H | $-C_6H_5$ | 8.41 | B 1 | 100 | 6800 | 5 | 0.2 |
| 36 | — | 23.22 | 51.30 | H | H | $-C_6H_5$ | 15.48 | F 10 | 100 | 9 | 3 | 0.2 |
| 37 | — | 34.46 | 56.94 | H | $CH_3$ | $-CO_2CH_3$ | 8.49 | A 0.1 | 100 | 5400 | 5 | 0.2 |
| 38 | — | 25.02 | 55.29 | H | $CH_3$ | $-CO_2CH_3$ | 16.68 | E 3 | 100 | 867 | 4 | 0.2 |
| 39 | — | 37.82 | 55.86 | H | H | $-Si(C_2H_5O)_3$ | 4.26 | A 2 | 100 | 977 | 4 | 0.2 |
| 40 | — | 33.46 | 55.29 | H | H | $-Si(C_2H_5O)_3$ | 8.24 | C 3 | 100 | 78 | 4 | 0.2 |
| 41 | — | 29.29 | 55.29 | H | H | $-Si(C_2H_5O)_3$ | 12.41 | B 3 | 100 | 163 | 4 | 0.2 |
| 42 | — | 24.25 | 53.58 | H | H | $-Si(C_2H_5O)_3$ | 16.16 | F 6 | 97 | 24 | 3 | 0.2 |
| 43 | — | 25.54 | 56.43 | H | H | $-N\overset{CH_2-CH_2}{\underset{CO-CH_2}{\diagup\diagdown}}$ | 17.02 | A 1 | 100 | 8293 | 5 | 0.2 | may also be used in the preparation of pharmaceutical compositions in the form of tablets, ointments and gels. Finally, the products of the invention may be used, due to their thickening effect in solvents, such as cetones, alcohols, chlorinated hydrocarbons and water, also for the preparation of so-called technical compositions on the basis of such solvents. Examples are car cleaners, engine cleaners and household detergents.

The quantitative proportion of the above-described thickening agents in the various compositions may vary, depending on the viscosity desired, between 0.05 and 3%, however, preferably between 0.5 and 2%, calculated on the weight of the finished formulation. The incorporation of the thickening agents into the solutions, suspensions or emulsions to be thickened is effected in known manner by dissolving in water and/or in the solvent-containing phase used at room temperature, optionally while heating and subsequently adding the other components.

The following Examples are to illustrate the possibilities of application of the polymer thickeners.

Liquid oil-in-water emulsion 0.2% of polymer prepared according to Example 1
3.0% of oleyl alcohol+5 mols of ethylene oxide
6.0% of isopropyl myristate
0.1% perfume oil
ad 100% water+preservative

Liquid oil-in-water emulsion 0.3% of polymer corresponding to Example 1
3.0% of distearyldimethyl ammonium chloride
6.0% of paraffin oil
6.0% of isopropyl palmitate
0.5% of cetyl alcohol
0.2% of perfume oil
ad 100% water+preservative

Oil-in-water cream 0.5% of polymer corresponding to Example 1
7.0% of trialkyl-tetraglycolether-o-phosphate
11.0% of paraffin oil
10.0% of isopropyl myristate
3.0% of sorbitol
ad 100% water+preservative

Water-in-oil cream 2.0% of polymer corresponding to Example 1
5.0% of diglycerol sesquioleate
6.0% of paraffin oil
0.2% of perfume oil
ad 100% water+preservative

Sun protective gel 1.0% of polymer corresponding to Example 1
40.0% of ethyl alcohol
3.0% of UV absorber
ad 100% water

After shave gel 1.0% of polymer corresponding to Example 1
40.0% of ethyl alcohol
0.3% of menthol
ad 100% water

Bracing gel 0.5% of polymer corresponding to Example 1
30.0% of ethyl alcohol
5.0% of isopropyl myristate
0.1% of perfume oil
ad 100% water

Insect protective cream 0.7% of polymer corresponding to Example 1
5.0% of polyoxethylene (20) sorbitane monostearate
10.0% of stearic acid
5.0% of isopropyl palmitate
20.0% of insect protective agent
0.2% of perfume oil
ad 100% water+preservative

Liquid hand lotion 0.2% of polymer corresponding to Example 1
5.0% of cetyl alcohol
5.0% of propylene glycol
0.1% of perfume oil
0.3% of isopropyl myristate
ad 100% water

Hand cleanser 1.4% of polymer corresponding to Example 1
12.0% of coconut oil acid-methyl tauride-sodium salt
2.0% of lauryldiglycol-ether sulfate-sodium salt
2.0% of polyethylene glycol (molecular weight 1000)
1.0% of sodium tripolyphosphate
35.0% of polyvinyl alcohol
0.1% of perfume oil
0.05% of formalin
ad 100% water

Hair shampoo with a pearly lustre effect 1.0% of polymer corresponding to Example 1
12.0% of coconut oil alcohol+10 mols of ethylene oxide
2.0% of triethylene-glycol distearate
0.2% of perfume oil
ad 100% water+preservative

Liquid make-up 0.5% of polymer corresponding to Example 1
3.0% of trilauryl-tetraglycol-ether-o-phosphate
5.0% of cetyl-stearyl alcohol
1.0% of oleic acid-monoethanolamide+5 mols of ethylene oxide
7.0% of isopropyl stearate
8.0% of paraffin oil
5.0% of pigment dyestuffs
5.0% of sorbitol
0.1% of perfume oil
0.1% of preservative
ad 100% water

Toothpaste 1.2% of polymer corresponding to Example 1
45.0% of dicalcium phosphate-dihydrate
0.5% of sodium-lauroyl sarcoside
0.3% of peppermint oil
20.0% of sorbitol
0.1% of saccharin
ad 100% water

Hair setting gel 2.0% of polymer corresponding to Example 1
2.0% of polyvinyl pyrrolidone
0.2% of perfume oil
40.0% of ethyl alcohol ad 100% water Transparent cleaning liquid 0.5% of polymer corresponding to Example 1
5.0% of polyethylene-glycol, molecular weight 400
10.0% of ethyl alcohol
2.0% of acylaminopolyglycol-ether sulfate-triethanolamine salt
0.1% of perfume oil
0.1% of preservative
ad 100% water Sulfur-containing ointment 1.5% of polymer corresponding to Example 1
15.0% of colloidal sulfur
ad 100% water Zinc oxide-containing ointment 1.2% of polymer corresponding to Example 1
10.0% of zinc oxide
ad 100% water Sodium salicylate-containing gel 1.4% of polymer corresponding to Example 1
5.0% of sodium salicylate
ad 100% water Boric acid gel 1.1% of polymer corresponding to Example 1
5.0% of boric acid
ad 100% water Graphite suspension 1.3% of polymer corresponding to Example 1
20.0% of graphite dust
ad 100% water Furniture polish 0.5% of polymer corresponding to Example 1
5.0% of silicon oil emulsion (30% strength)
3.0% of carnauba wax emulsion (20% strength)
ad 100% water Car tire cleanser 1.2% of polymer corresponding to Example 1
20.0% of isopropyl alcohol
10.0% of nonylphenol + 10 mols of ethylene oxide
ad 100% water Glycerol gel 1.0% of polymer corresponding to Example 1
40.0% of glycerol
ad 100% water Titanium dioxide suspension 0.4% of polymer corresponding to Example 1
55.0% of titanium dioxide (powder)
ad 100% water

What is claimed is:

1. Cosmetic, pharmaceutical and technical compositions containing as a thickening agent cross-linked polymers whose polymer chains show the following composition:

k-p molar % of groups of the formula

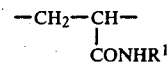

p molar % of groups of the formula

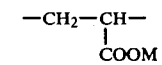

from 0 to 45 molar % of groups of the formula

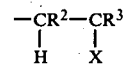

and
from 0.1 to 20 molar % of a cross-linking agent, wherein
$R^1$ represents as a statistical mean value from 0 to 100 molar % of hydrogen and from 100 to 0 molar %, each calculated on the proportion of (k-p) molar %, of $CH_2OH$ groups,
$R^2$ and $R^3$ are hydrogen, or one of the radicals $R^2$ and $R^3$ is methyl, the other being hydrogen,
X is cyano, alkoxycarbonyl with from 1 to 8 carbon atoms altogether, whose alkoxy radical may also be substituted by —OH, alkanoyloxy with from 2 to 6 carbon atoms, alkanoylamino with 2 to 8 carbon atoms which—if they have at least 4 carbon atoms—may also be cyclic and then form a pyrrolidone or caprolactam ring, phenyl, carboxyl or trialkoxysilyl with 1 to 2 carbon atoms in the alkoxy groups,
M is an alkali metal cation, and
k stands for the range of from 99.9 to 50,
p stands for the range of from 5 to k,
said products being prepared by copolymerizing, calculated on the total molar amount of all monomers,
k molar % of acrylamide, k being defined as above,
from 0 to 45 molar % of a compound of the formula I

in which $R^2$, $R^3$ and X are defined as above, and from 0.1 to 20 molar % of a cross-linking agent in the presence of a radical initiator in a water-miscible alkanol solution, subjecting the polymer paste obtained to strong shearing forces until a uniform flow behavior of the suspension is achieved, mixing said polymer suspension under the action of strong shearing forces with p molar % of an alkali metal hydroxide of the formula MOH, p being defined as above, heating the mixture at a temperature of from 30° to 150° C. up to the saponification of p molar % of amide groups to form —COOM— groups, and either isolating the copolymer obtained or methylolating the same, after removing the ammonia, in a lower alkanol with from 0 to (k-p) molar % of paraformaldehyde, k and p being defined as above, at a temperature of from 10° C. to the boiling point of the lower alkanol employed.

2. Compositions as claimed in claim 1 containing a cross-linked polymer which contains as comonomer a monomer of the formula

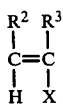 (I), in which
R² is hydrogen,
R³ is hydrogen or methyl and
X is cyano, alkoxycarbonyl with from 1 to 8 carbon atoms in the alkoxy radical which may also be substituted by —OH, or X is acetoxy, N-pyrrolidonyl, phenyl or triethoxysilyl.

3. A composition as claimed in claim 1, which contains a polymer which is cross-linked by a compound of the formula

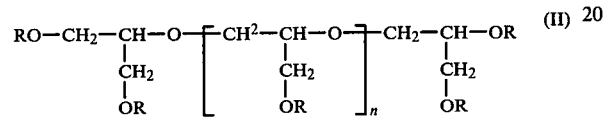 (II)

in which
n stands for a number of from 0 to 30, and
R is hydrogen for 70 to 5% and stands for groups of the formulae —CH₂—CH=CH₂ or —CH₂—C(CH₃)=CH₂ for 95 to 30%.

4. A composition as claimed in claim 1, which contains a cross-linked polymer containing from 0 to 20 molar % of a comonomer of the formula

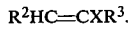

5. A composition as claimed in claim 1, which contains a cross-linked polymer being free of a comonomer of the formula

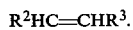

6. A composition as claimed in claim 1, which contains a cross-linked polymer cross-linked with 1 to 2 molar % of the cross-linking agent.

7. A composition as claimed in claim 1, which contains a cross-linked polymer, wherein p represents a number of from 30 to 70.

8. A composition as claimed in claim 1, which contains a cross-linked polymer which is methylolated with from 0.8 (k-p) to 1 (k-p) molar % of paraformaldehyde.

* * * * *